US007012042B1

(12) United States Patent
Cataldo et al.

(10) Patent No.: US 7,012,042 B1
(45) Date of Patent: Mar. 14, 2006

(54) METHODS AND PRODUCTS TO PROTECT AGAINST ROOT INTRUSION AND PLANT AND ROOT GROWTH

(75) Inventors: Dominic A. Cataldo, Kennewick, WA (US); Edward S. Lipinsky, Worthington, OH (US); Peter Van Voris, Alexandria, VA (US); Daren L. Beck, Salem, OR (US); Richard Beck, Salem, OR (US)

(73) Assignee: Growguard, LLC, Inc., Kenniwick, WA (US)

( * ) Notice: Subject to any disclaimer, the term of this patent is extended or adjusted under 35 U.S.C. 154(b) by 0 days.

(21) Appl. No.: 10/438,559

(22) Filed: May 15, 2003

Related U.S. Application Data

(60) Provisional application No. 60/380,584, filed on May 15, 2002.

(51) Int. Cl.
*A01N 25/34* (2006.01)
*A01N 33/18* (2006.01)
*D01F 1/02* (2006.01)

(52) U.S. Cl. ..................................... 504/347; 264/211
(58) Field of Classification Search ................ 504/347; 264/211
See application file for complete search history.

(56) References Cited

U.S. PATENT DOCUMENTS

| 5,003,726 A | * | 4/1991 | Allport ........................ 405/43 |
| 5,096,206 A | * | 3/1992 | Andre et al. ................. 277/314 |
| 5,116,414 A | * | 5/1992 | Burton et al. ................ 504/347 |
| 5,139,566 A | * | 8/1992 | Zimmerman ................. 504/361 |
| 5,898,019 A | * | 4/1999 | Van Voris et al. .......... 504/360 |

* cited by examiner

*Primary Examiner*—S. Mark Clardy
(74) *Attorney, Agent, or Firm*—Mueller and Smith, LPA

(57) ABSTRACT

One aspect of the present invention is a sprayable composition for coating pipe for protecting it from one or more of root intrusion or root growth when the coated pipe is placed underground. Such sprayable formulation includes a 2,6-dinitroaniline herbicide; a polymer pellet impregnated with a 2,6-dinitroanililne herbicide-sorbed colloidal clay; and a film-forming polymer. Another aspect is pipe coated with the dried residue of a coating of a 2,6-dinitroaniline herbicide; a polymer pellet impregnated with a 2,6-dinitroaniline herbicide-sorbed colloidal clay; and a film-forming polymer, wherein the coated pipe is protected from one or more of root intrusion or root growth when the coated pipe is placed underground.

21 Claims, 10 Drawing Sheets

SEWER PIPE CONCEPT

FIGURE 1. SEWER PIPE CONCEPT

Acrylimide Gel Release Data

□    Water
◇    Water+WA

Extraction Time
(days)

Figure 2

Release rate profiles for TRIFLURALIN contained within
PE granules associated with Acrylimide Gel.

Longevity versus PE or PU Loading

PE/PU Loading (% w/w)

□ PE Longevity
◇ PU Longevity

Figure 3
Relationship between Acrylimide Gel Longevity and concentration of PE/TRIFLURALIN and PU/TRIFLURALIN carrier. Values assume a 25% duty cycle, and show a 20% variation due to uncontrolled variables.

Figure 4 - UNSATURATED POLYESTER BARRIER COATING CONCEPT

FIGURE 5– EPOXY RESIN BARRIER COATING CONCEPT

FIGURE 6 - GEOTEXTILE SYSTEM

Vapor Pressure/Air Transfer from Cord to Receiving Solution)

☐ Water + Tween
◇ Methanol (80%)

Days of Transfer

Figure 7

Vapor transfer of TRIFLURALIN from delivery cord/reservoir to receiving solutions.

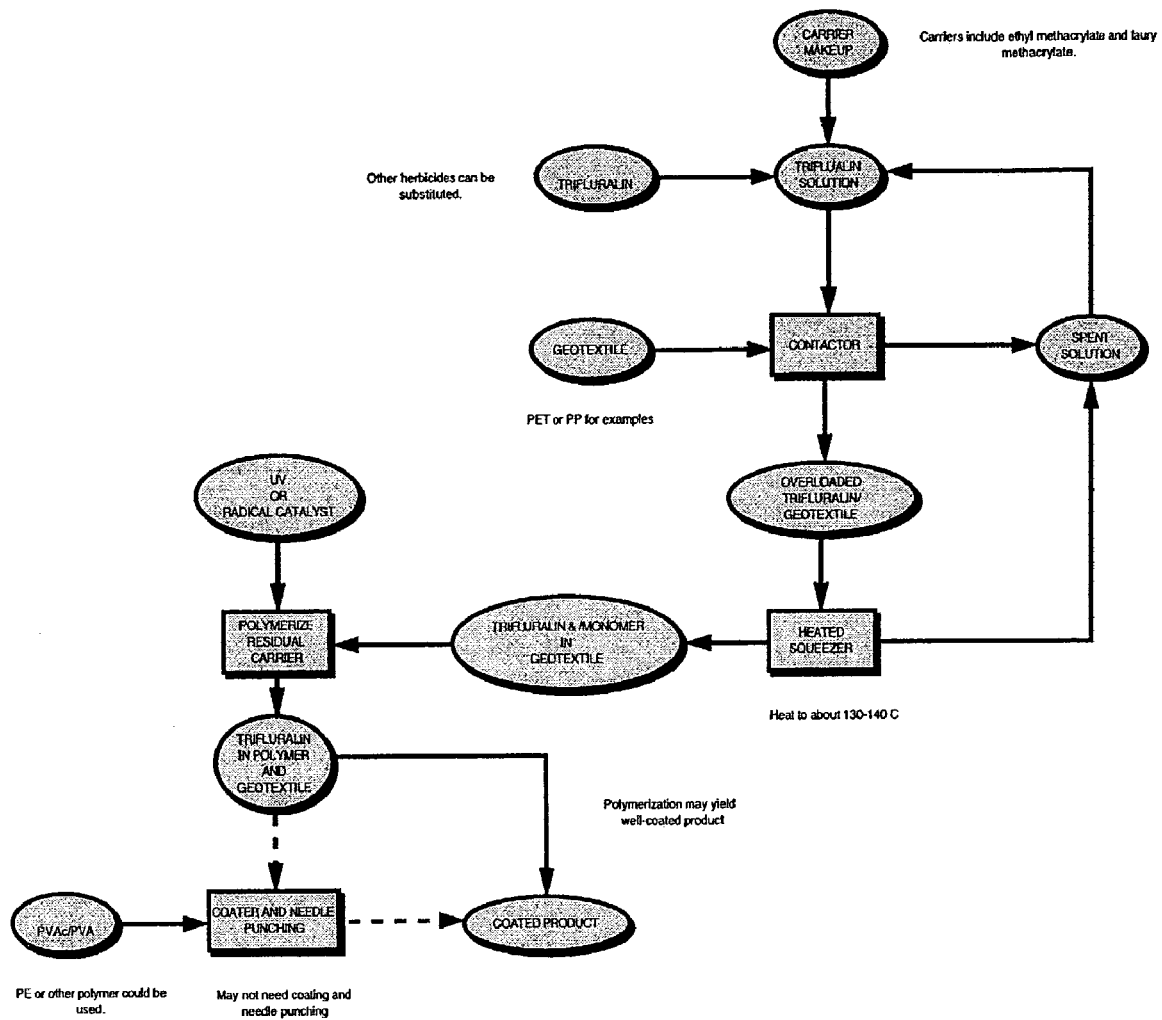
FIGURE 8- IPN GEOTEXTILE SYSTEM

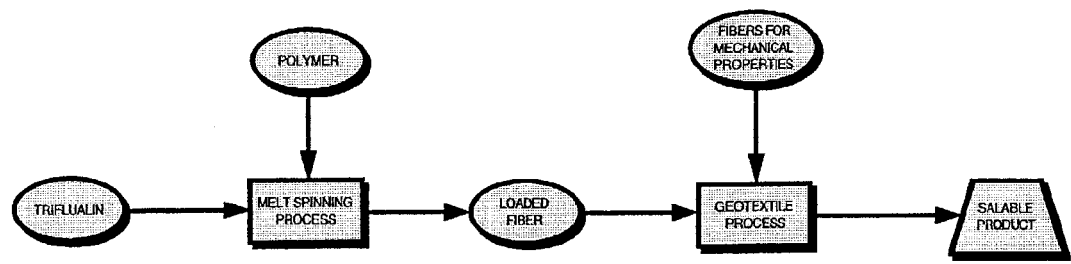
FIGURE 9 POLYMER AND TRIFLURALIN MELT SPINNING

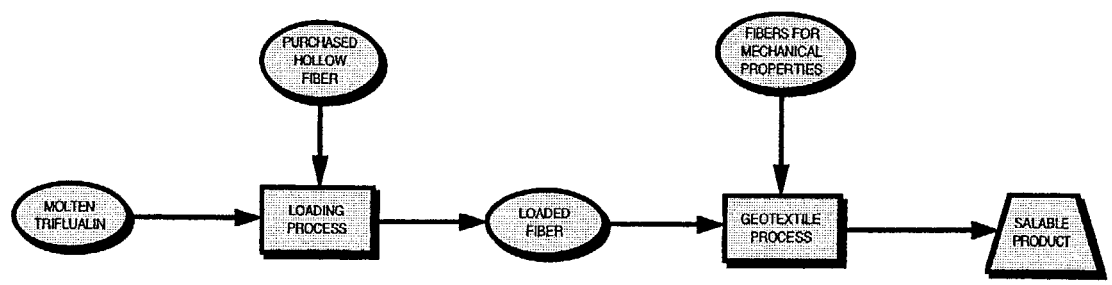
FIGURE 10- HOLLOW FIBER CONCEPT

METHODS AND PRODUCTS TO PROTECT AGAINST ROOT INTRUSION AND PLANT AND ROOT GROWTH

CROSS-REFERENCE TO RELATED APPLICATIONS

This application claims benefit of provisional application Ser. No. 60/380,584, filed May 15, 2002, the disclosure of which is expressly incorporated herein by reference.

STATEMENT REGARDING FEDERALLY SPONSORED RESEARCH

Not applicable.

BACKGROUND OF THE INVENTION

The present invention generally relates to protecting against unwanted root intrusion, plant growth, and root growth, and more particularly new methods and products for accomplishing same.

Roots from trees and shrubs are known to cause a variety of problems as well as damage to man-made infrastructure. For example, sanitary and storm drain systems in cities and other municipalities are aging with part of the problem induced by the roots of trees. The aging process involves physical cracks and joint dislocations, resulting in leakage of sewage and storm waters to soils, ground waters, and surface waters. A number of remedial relining methods are available. These work for a short period and are then degraded by plant roots seeking out moisture and nutrients, entering the lines, dislocating and degrading the linings, and thus creating the original problem. To counter this problem of plant-root intrusion, options have been used whereby liquid herbicide is simply flushed through the sewer lines or the sewer line is wrapped with a herbicide releasing fabric; however, the later needs to be done when the sewer line has been dug up for repairs or when new sewer lines are being laid.

New products and methods are needed to control the intrusion of roots not only into sewer and other pipes, but also into sidewalks, golf course areas, especially greens. The new methods and products also could be used to control weed growth in landscaping situations.

For piping systems, these methods and products should offer reduced transport of herbicide into the environment and reduced disturbance of the piping system. For sidewalks, golf courses, landscapes, etc., application of the product should disrupt the system rarely.

To meet these environmental and minimal-disruption requirements, the new products will make use of the ability of Trifluralin and related chemical compounds to stop roots from growing, thus repelling roots without necessarily killing the plants. The key difference between the new products/methods and conventional ones is sustained performance, usually over many years of product life.

Commercial applications for the new products include those cited above, plus control of plant/root growth in landscaped areas, roadside gravel areas, planter strips, stone walkways, brickwork patios and driveways. Soil stabilization can be achieved along with root control. These products can be applied during construction or in remedial situations.

ART

The following art has relevance to this invention as summarized below.

1. U.S. Pat. No. 5,069,706 proposes to flush a sewer line with a mixture of an organic herbicide, carbonate, and foam producing surfactant to inhibit flora growth.
2. U.S. Pat. No. 5,003,726 proposes to inhibit root growth around outlets of drip irrigation hose by introducing clay or the like into the line followed by a herbicide. The clay absorbs the herbicide for providing root growth protection.
3. U.S. Pat. No. 4,981,524 proposes a method to coat the upper inside of pipe with root-inhibiting foam.
4. U.S. Pat. No. 4,988,236 proposes a biocide containing tape for application to underground pipe.
5. U.S. Pat. No. 4,025,360 proposes an apparatus to coat the inside of pipe with foam.
6. U.S. Pat. No. 5,165,434 proposes an apparatus for blowing dry herbicide inside underground pipe.
7. U.S. Pat. No. 5,735,955 proposes an apparatus to coat the inside of pipe with foam.
8. U.S. Pat. No. 4,405,360 proposes to incorporate a porosigen (having a water solubility of between about 0.0005 and 100 g per 100 g of $H_2O$) into a thermoplastic and/or thermoset polymer and herbicide to form a controlled release herbicide dispenser. Porosigens form pores by dissolving in water. The result is a growing tube structure that taps active ingredient that is stored in the matrix.
9. U.S. Pat. No. 4,284,444 proposes to prepare anti-bacterial, anti-fungal, etc., non-porous polymeric preforms by adhering a non-porous layer of a polymeric composition containing an anti-bacterial, anti-fungal, etc. agent that is capable of migrating into said preform so that such migration takes place. For example, a PVC preform has a $PVC/CaCO_3/DOP$ containing tri-n-butyl tin neodecanoate layer adhered to the preform for permitting the tin compound to migrate into the PVC preform.
10. U.S. Pat. No. 3,891,423 proposes a weed growth retardant product for woody plants of a sheet-like water-permeable fabric substrate (e.g., cotton, rayon, nylon, polyethylene, polypropylene) having adhered thereto a very slightly water-soluble film-forming binder (e.g., vinyl resins, insolubilized carbohydrates, aminoplast resins, insolubilized proteins, polyesters, polyethers, polyamides, polyurethanes) and a herbicide.
11. U.S. Pat. No. 3,096,167 appears to be a very early proposal for making biotextiles in that this patent generically claims incorporating a water-leachable, soil sterilant into a non-rigid fibrous carrier.
12. U.S. Pat. No. 4,360,376 proposes a very specific Pennwalt interfacial condensation polymerization system of microencapsulation.
13. U.S. Pat. No. 4,439,488 proposes encapsulation that uses aqueous gel formation as a key step.
14. U.S. Pat. Nos. 5,073,191, 5,160,530, and 5,317,004 propose an aqueous emulsion approach in which trifluralin is dispersed in a molten state. The capsules contain very small particles (down to 0.1 micron). Spray drying is involved. The polymorphism of trifluralin is exploited in these inventions.
15. U.S. Pat. No. 5,980,996 proposes to control of water flow, which is irrelevant to our goals. However, the method uses UV radiation to polymerize acrylates that can be partly neutralized and, thus, can be ionomers (although not identified as such in the patent). The substrates include our favorite fibers, but the penetration of monomer into the fiber does appear to be appreciated by the inventors. The use of the structure to hold compounds other than water also is not appreciated.

16. U.S. Pat. No. 3,676,441 proposes a specific class of chemicals. The specification, however, presents a number of ideas for making granules. The active ingredient can be mixed with polymerizable substances that are polymerized under conditions that do not affect the active ingredient. A prepared porous polymer is impregnated with a solution of the active ingredient followed by removal of the solvent.

17. U.S. Pat. No. 4,731,143 tells how to coat a geotextile with a thin polymer film. This patent does not mention active ingredients. This patent limits the polymer film to being an aqueous dispersion.

18. U.S. Pat. No. 5,389,432 tells how to deposit a binder selectively on the places where the fibers overlap while leaving the rest of the fabric mostly uncoated. This overlap-only feature could be useful for economizing on expensive active ingredients.

19. U.S. Pat. No. 5,534,304 describes how to cause a fabric to have extremely long flow-through times (90 days vs. 1 minute which is 129,600 to 1). Superabsorbent materials that are used to attain this result include polyacrylic acids, polyacrylamides with cross-linking via metal ions. These are not the same as ionomers. The super absorbent materials are applied as water-in-oil emulsions. The structures that are desired for this invention are tailored to sorb and hold water tenaciously.

20. U.S. Pat. Nos. 5,614,256 and 5,736,466 pertains to watertight, vapor-permeable, and flame-retardant coatings. The key steps are to make a stable foam from the blended ingredients, apply the foam to a fabric (geotextile), and then convert the foam into a continuous coating with the desired properties.

21. U.S. Pat. No. 5,942,006 is limited to cellulosic fabrics and a polymerizable organophosphate flame retardant. However, some claims include blends of cellulosic and synthetic fibers.

22. Japanese Patent No. 401221573A proposes to coat polypropylene fabric with an unsaturated carboxylic acid or its derivative, then irradiate with high energy beams followed by coating the fabric with a monomer then irradiating the solution with active high energy beams to effect graft modification.

23. Japanese Patent No. 401198346A proposes to impregnate a polyethylene net with acrylic acid and sodium hydroxide and irradiate with an electron beam to form a water absorbable sheet.

24. U.S. Pat. No. 5,116,414 and its division, U.S. Pat. No. 5,449,250, propose incorporating a herbicidal 2,6-dinitroanaline into a polymer to form a device, which is placed beneath the soil to release the 2,6-dinitroanaline over time.

25. U.S. Pat. No. 5,856,271 proposes to blend an active chemical (herbicide) with a moisture-free carrier (carbon black) and add the resulting product to a polymer preform, which then is formed into a release device.

26. U.S. Pat. No. 5,181,952 proposes a geotextile having discrete spaced apart nodules of carbon black and 2,6-dinitroanaline herbicide.

27. U.S. Pat. No. 5,898,019 proposes to fill cracks in pavement with a first polymer containing a pre-emergent herbicide and with a second polymer containing a systemic herbicide, and then hot seal coating the crack.

28. U.S. Pat. No. 5,139,566 proposes a geotextile having spaced-apart nodules formed from a liquid mixture of herbicide and binder, which mixture is injected into the geotextile.

29. U.S. Pat. No. 5,620,499 proposes a shaped water insoluble elastomer containing a fertilizer that releases the fertilizer at a controlled rate.

30. U.S. Pat. Nos. 5,883,046 and 5,733,848 produce microparticles of a rapidly leaching agrochemical within a polymer matrix of a cross-linked unsaturated polyester/vinyl polymer by forming a NAD of the agrochemical, unsaturated polyester, and vinyl ester resin followed by polymerization.

31. U.S. Pat. No. 5,985,010 proposes an animal repellent of capsicum and at least one liquid organic solvent in a cross-linked polymer resin.

32. U.S. Pat. No. 5,866,141 proposes to coat a polymer fabric with an agrochemical in admixture with an adhesive for application to a plant.

33. U.S. Pat. No. 5,130,342 proposes microporous thermoplastic polymeric articles (including fibers) that are particulate filled.

34. U.S. Pat. No. 5,093,197 proposes hollow fibers formed from ultra-high molecular weight polyolefin, which can be woven into fabric.

35. U.S. Pat. No. 6,150,019 proposes hollow polymeric fibers than can contain a dye.

36. U.S. Pat. No. 5,801,194 establishes the technical feasibility for epoxy resins as barrier coatings with several pesticides.

37. U.S. Pat. No. 6,099,850 proposes mixing an insecticide with a polymer to form a controlled release barrier.

38. U.S. Pat. No. 5,985,304 establishes the technical feasibility for epoxy resins as barrier coatings with several pesticides.

BRIEF SUMMARY OF THE INVENTION

One aspect of the present invention is a sprayable composition for coating pipe for protecting said coated pipe from one or more of root intrusion or root growth when said coated pipe is placed underground. Such sprayable formulation includes a 2,6-dinitroaniline herbicide; a polymer pellet impregnated with a 2,6-dinitroanililne herbicide-sorbed colloidal clay; and a film-forming polymer. Another aspect is pipe coated with the dried residue of a coating of a 2,6-dinitroaniline herbicide; a polymer pellet impregnated with a 2,6-dinitroaniline herbicide-sorbed colloidal clay; and a film-forming polymer, wherein the coated pipe is protected from one or more of root intrusion or root growth when the coated pipe is placed underground. As another aspect, an inflatable bladder can be coated with a coating of a 2,6-dinitroaniline herbicide; a polymer pellet impregnated with a 2,6-dinitroanililne herbicide-sorbed colloidal clay, and hung inside a pipe to protect it from one or more of root intrusion or root growth.

In a formulation of one or more of a polymer gel for repairing pipe, a grout for pipe, or a soil stabilizer, the improvement for one or more of root intrusion or root growth when said coated pipe is placed underground, is achieved by incorporating into the formulation, a 2,6-dinitroaniline herbicide and a polymer pellet impregnated with a 2,6-dinitroanililne herbicide-sorbed colloidal clay.

Improved geotextile fabric or landscape type fabric can be produced by incorporating into the fabric a formulation of a 2,6-dinitroaniline herbicide and a polymer pellet impregnated with a 2,6-dinitroanililne herbicide-sorbed colloidal clay.

Another aspect is an improved method for filling gaps in pavement for repelling unwanted invasion by plants by filling the gaps with a polymer matrix in which is dispersed a composite formed from a colloidal clay, a 2,6-dinitroaniline herbicide, and polymer composite.

Yet another aspect is an improved grout or gasket capable of repelling unwanted invasion by plants, which grout is an elastomer matrix in which is dispersed a composite formed from a colloidal clay and a 2,6-dinitroaniline herbicide.

Yet another aspect is a method for protecting pipe from one or more of root intrusion or root growth when said pipe is placed underground, includes the steps of infusing a cord with a 2,6-dinitroaniline herbicide-sorbed colloidal clay and hanging said infused cord inside said pipe, whereby vapors released from said infused cord protect said pipe from one or more of root intrusion or root growth.

Yet another aspect is a melt spinning process for manufacturing a geotextile wherein molten fiber-containing polymeric material is melt spun using spinnerets. This process includes blending particles bearing a 2,6-dinitroaniline herbicide-sorbed colloidal clay with a melt said polymeric material, the size of said particles allowing the blend to be melt spun.

Yet another aspect is an improved geotextile fabric wherein incorporated into said geotextile fabric is a formulation of hollow fibers containing a 2,6-dinitroaniline herbicide.

Yet another aspect is an improved geotextile fabric wherein the 2,6-dinitroaniline is incorporated into the fibers of the polymeric fabric after the fibers have been formed by soaking the fibers in a molten blend of the 2,6-dinitroaniline colloidal clay mixture.

ADVANTAGES OF THE INVENTION

This invention protects a territory from intrusion by roots of plants. It does so by repelling the roots, rather than killing the plant. It thus has ecological advantages over conventional herbicide root control methods that kill the plant. This consideration is important for protection of golf course greens against encroachment by trees that are needed as hazards, for example.

The products of this invention have a wide scope of application that includes soil stabilization with root control, decorative landscapes, roadside plantings, parks and playgrounds. The products save the user significant expenditures of labor that would be needed for repeated applications of less sustainable products.

The products of this invention can be installed once and used for many years. This saves the cost of materials and labor that would be devoted to repeated installations. It also avoids repeated disruption of the ground.

The slow release of Trifluralin into the environment not only reduces environmental damage, it also saves money and resources because less active ingredient is consumed.

Conventional herbicide applications lead to leaching and damaging runoff, which are avoided by use of this sustained release system. Thus, drinking water resources are protected.

Application of conventional herbicides can expose to toxicity dangers those who apply the herbicide. Other people and pets in the vicinity are also placed at risk. This sustained release system minimizes such risks.

The pipe embodiment is especially useful because the coating can resist biodegradation that occurs in sewers and other environments that contain diverse biotic species. The polyurethane formulations of this invention resist biodegradation by selection of appropriate polymers and by means of additives.

The barrier coatings of this invention include unsaturated polyesters and epoxy resins that are inexpensive and highly resistant to biological attack due to their crosslinked chemical structures. These materials are also strong and resist degradation due to weathering. These polymers thus contribute to the sustained performance of the products of this invention.

BRIEF DESCRIPTION OF THE DRAWINGS

For a fuller understanding of the nature and advantages of the present invention, reference should be had to the following detailed description taken in connection with the accompanying drawings, in which:

FIG. 2 graphically plots release rate profiles for Trifluralin contained within polyethylene (PE) granules associated with Acrylimide Gel;

FIG. 3 graphically plots the relationship between Acrylimide Gel Longevity and concentration of PE/Trifluralin and PU/Trifluralin carrier, wherein the values assume a 25% duty cycle, and show a 20% variation due to uncontrolled variables;

FIG. 7 graphically plots vapor transfer of Trifluralin from delivery cord/reservoir to receiving solutions;

FIG. 8 schematically depicts the manufacturing steps for the IPN geotextile embodiment of the present invention;

FIG. 9 schematically depicts the manufacturing steps for the polymer/Trifluralin melt spinning embodiment of the present invention; and FIG. 10 schematically depicts the manufacturing steps for the hollow fiber embodiment of the present invention.

The drawings will be further described below.

DETAILED DESCRIPTION OF THE INVENTION

The root intrusion problems that affect sewer systems, sidewalks, golf courses, etc., can be treated effectively with herbicides. However, conventional sewer treatment only lasts for a few days or weeks. Most conventional systems for delivery of Trifluralin for appreciable lengths of time generate environmental burdens in the form of contamination of ground water. The few exceptions (e.g., BioBarrier I and II) are not suitable for application to pipes and other substrates of this invention.

Sustained release systems are needed that keep the roots away for years. Trifluralin is an outstanding herbicide for these uses, but the suggested embodiments could be applied to other 2,6-dinitroaniline herbicides and many other types of herbicides. In this patent application, the term "TRIFLURALIN" includes other 2,6-dinitroaniline herbicides and other root-growth/repellent herbicides.

The four inventive embodiments are:

1. Protect pipes (sewer, gray-water, storm) and pavement with sustained release formulations that contain TRIFLURALIN.

2. Manufacture geotextile fabrics are loaded with Trifluralin and have barrier coatings.
3. Load geotextile fabrics with Trifluralin after manufacture.
4. Load fibers with Trifluralin before they are used to manufacture geotextile fabrics.

Embodiment #1

Pipe and Pavement Protection

Protect sewer, gray-water, and storm system pipes from root intrusion by application of a coating that contains TRIFLURALIN. All types of pipe that can come in contact with roots are included, especially sewer pipes, irrigation pipes, storm water pipes, water pipes, and drain-vent-and-waste pipes. There are three distinct approaches to this embodiment.

Spray-Applied Sustained-Release Coatings

Figure 1:
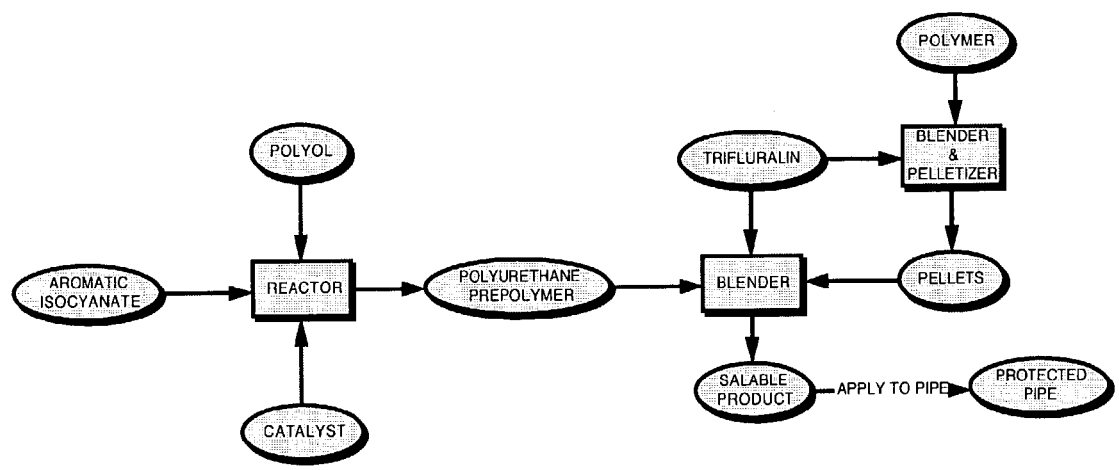
FIG. 1 schematically depicts the manufacturing steps for the sewer pipe embodiment of the present invention.

The apparatus that is the subject of General Chemical Company's U.S. Pat. No. 5,735,955 is a device that is used commercially. Thus, the embodiment of spraying material inside the sewer pipes is practical. The drawback of the current product is that it does not provide sustained protection from root penetration. The product of this invention is designed to overcome this drawback, as illustrated in FIG. 1. As shown in FIG. 1, a polyurethane prepolymer is prepared by reaction of an aromatic isocyanate (e.g., MDI) with a polyol. The prepolymer is mixed with Trifluralin-sorbed clay. By "Trifluralin-sorbed colloidal clay" or "2,6-dinitroaniline herbicide-sorbed colloidal clay" is meant colloidal clay particles sorbed with Trifluralin or a 2,6-dinitroaniline herbicide. Such sorbed colloidal clay particles even may be referred to as a colloidal clay-Trifluralin blend or mixture. Pellets are made from a molten polymer in which is dispersed Trifluralin-sorbed colloidal clay particles. The Trifluralin-loaded pellets are mixed with the Trifluralin-loaded polyurethane prepolymer. This product is applied to a pipe or other substrate by spraying with a catalyst so that the prepolymer cures to be a polymeric source of Trifluralin.

Previous work by Cataldo and Van Voris (U.S. Pat. Nos. 5,019,998, 5,116,414, 5,181,592, 5,449,250, 5,744,423, and 5,744,423) and Van Voris, P., D. A. Cataldo, C. E. Cowan, N. R. Gordon, J. F. Cline, F. G. Burton and W. E. Keiens. 1988, "Long-Term Controlled Release of Herbicides: Root Growth Inhibition"; *Pesticide Formulations, Innovations and Developments*, eds. B. Cross and H. G. Scher, pp. 222–240; ACS Symposium Series 371, American Chemical Society, Washington, D.C.; D. A. Cataldo, E. S. Lipinsky, and P. Van Voris, 1999, "Long-Term Controlled-Release Pesticide Devices"; *Controlled-Release Delivery Systems for Pesticides*, Ed. Herbert B Sher, Marcel Dekker, Inc., New York, has shown that Trifluralin can be effective in prevention of root intrusion in soil environs for several decades. Polyurethane products, similar to those contained in this embodiment, demonstrated sustained release. The differences between the current embodiment and prior art is the use of a spray method to apply a polymer product that adheres to the sewer pipe in which the herbicide is dispersed both in the polyurethane and in plastic pellets that form part of the polymer product and exposure of the polyurethane product to sewage. A combination of Trifluralin neat and Trifluralin-containing polymer pellets is dispersed in a coating formulation and spray applied to the inside of pipe to form a durable coating that exhibits a dual release of Trifluralin.

A preferred polymer coating is polyurethane. By "polyurethane", we mean the various polymers made by reaction of isocyanates with polyols, water, and other hydrogen donors. The polymers can have urea linkages, biuret linkages, allophanate linkages, carbodiimide linkages, and free isocyanates groups.

Other sprayable polymers are included in this invention, as described in Embodiment #2. Because of the intense microbial activity of the contents of sewers, it is essential for the design of the polyurethane focus on chemical structures that do not degrade over the life of the product. Resistance to microbial attack can be attained by use of selected isocyanates (e.g., aromatics) and polyols (e.g., sterically hindered ones) for production of the polyurethane and/or addition of agents that control microbial populations (e.g., bactericides).

EXAMPLE 1

In this example, sustained release of Trifluralin was demonstrated. Technical grade Trifluralin was loaded into thermoplastic urethanes at rates of 10–20% (w/w) without noticeable loss in polymer structure. Urethane loading and release rates were as follows: thermoplastic polyurethane released at a rate of 6 $\mu$g cm2/day when loaded to a 10% level. A casting urethane that was loaded with 10% Trifluralin released at 0.5 $\mu$g/cm$^2$/day.

Estimated longevity without additional barrier could be 20 years. Use of the pellets could extend this longevity considerably.

EXAMPLE 2

The table below shows data obtained by loading polypropylene (PP), polyethylene (PE), and polyethylene terephthalate (PET) with Trifluralin at the indicated levels and exposing them to a test environment. The loading operation involved mixing the melted thermoplastics with Trifluralin and then injection molding them.

| Material | Loading | Release |
| --- | --- | --- |
| PP | 20–25% | 21 $\mu$g/cm$^2$/day |
| PE | 20–25% | 38 $\mu$g/cm$^2$/day |
| PET | 10–15% | 2.5 $\mu$g/cm$^2$/day |

Pellets

The pellets of this invention that contain Trifluralin (see FIG. 1) can be made, for example, of a polyethylene (HDPE, LDPE, or LLDPE), polypropylene, polyesters (e.g., polyethylene terephthalate), rubber (natural or synthetic), nylon (Nylon 6, Nylon 66, or Nylon 610), colloidal clays (e.g., montmorillonite or bentonite), silicones, lactic acid polymers, cellulosic polymers (cellulose, cellulose acetate, cellulose acetate butyrate, carboxymethyl cellulose, hydroxypropyl cellulose), lignin, and polyurethanes (thermoplastic and thermoset), including water-curable polyurethanes.

Bladder Embodiment

Another embodiment of Embodiment #1 uses an inflatable bladder to create a small space near the wall of the pipe. The acrylimide gel or urethane formulation that contains very small Trifluralin pellets is pumped into place and polymerized. The result can be a chemical grouting that is applied to joints and cracks. Alternatively, the result could be an interior coating that is applied over selected lengths of the pipe.

This bladder method is currently used to kill roots in the interior of pipes. But the embodiment of using this system for sustained release of Trifluralin is novel. Also, the uses as a long lasting chemical grouting, discontinuous or continuous coating is novel.

Gel Repair Formulations

Polymer gels can be formulated to contain pellets of Trifluralin so that root intrusion can be prevented for extended periods of time. These gel products are especially useful in pipe repair. However, the scope of this application also extends to grouts and soil stabilization uses.

When special catalysts are used to cure acrylamide resins, a crosslinked product is formed that is named "Acrylimide gel". The current state of the art includes dispersion of Trifluralin in this gel so that it can be used to repair cracks in pipes while providing root-repellent properties. This product is of limited use because the Trifluralin escapes too soon. This invention includes Acrylimide gel repair formulations in which the Trifluralin is contained in polymeric pellets for sustained release of this root repellent. The formulation also contains some Trifluralin in the gel phase so that the product begins its protection immediately.

EXAMPLE 3A

The preparation of two types of gels that contain polymeric TRIFLURALIN-loaded polymeric pellets is described in this example.

Acrylimide gels were prepared by mixing 1 part acrylimide to 1 part crosslinking catalyst. Microthene polyethylene (PE) pre-absorbed with Trifluralin was mixed into the acrylimide immediately prior to mixing with catalyst. The loading rate of polymer/Trifluralin into gel was 5.5% (w/v). Analysis of the PE reservoir indicated a Trifluralin loading rate of 7.02% (w/w). This amounts to 3.9 mg Trifluralin per $cm^3$ gel, or a total Trifluralin content of 0.39% (w/w). Cubes, approximately 3 $cm^3$, of the acrylimide gel were cut from the formed gel. These were placed into 200 mL of either water or water plus 0.1% Tween 20 (a wetting agent, denoted in the figures and tables as "WA"). The latter optimized release and solubility of TRIFLURALIN. All studies conducted at 19–21° C.

Acrylimide gels were prepared by mixing 1 part acrylimide to 1 part catalyst. Thermoplastic polyurethane powders (PU) pre-absorbed with Trifluralin was mixed into the acrylimide immediately prior to mixing with catalyst. The loading rate of polymer/Trifluralin into gel was 5.5% (w/v). Analysis of the PU reservoir indicated a Trifluralin loading rate of 10.7% (w/w). This amounts to 5.9 mg Trifluralin per $cm^3$ gel, or a total Trifluralin content of 0.59% (w/w). Cubes, approximately 3 $cm^3$, of the Acrylimide gel were cut from the formed gel.

EXAMPLE 3B

This example provides data on exposure of the samples to simulated environments. The samples were placed into 200 mL of either water or water plus 0.1% Tween 20 (a wetting agent, denoted in the figures and tables as "WA"). This agent optimized release and solubility of TRIFLURALIN. All studies conducted at 19–21° C.

These sample treatments were monitored for release rates over a 50-day period, to remove any fast release components, and to determine time to steady state. Release rates over this period ranged from 21 µg/day to 9 µg/day Trifluralin released/day for the water solution system, and 87 µg to 50 µg/day for the water plus WA. After the 7-day pre-extraction period, samples were transferred to fresh solutions and the release rates monitored over 50 days.

FIG. 2 provided the plots for the time dependent release rates for the two treatments between 2 and 50 days. For the water plus WA treatment release rate declined over the 7-day period to 8.9 µg TRIFLURALIN/day; for the water treatment release rates declined to 4.7 µg/day at day II. In both instances, the final release rates appear to at or near, steady state, indicating that the values can be used in subsequent performance calculations.

Release rates for the PU based TRIFLURALIN, were 3.2 and 6.6 µg TRIFLURALIN/day at steady state (5 days) for the water-only and the water/WA treatments, respectively.

EXAMPLE 3C

Using the raw release rate figures, and based on the amount of Trifluralin contained in the PE/Trifluralin load, performance behavior for the acrylimide gel system can be roughly estimated. The total release rate profile and the amount of total Trifluralin within the gel reservoir were used estimate the longevity under the "worst" conditions. For the water-alone system, estimated longevity was found to be 2029 days or 5.5 years. For the more stringent scenario where there is solubility enhancers within the flowing waters (i.e., soaps, wetting agents, etc.), the longevity drops to 1214 days or 3.3 years.

Longevity of a sustained-release device/system is controlled by the size of the reservoir, and the overall release rate of active per unit time from the reservoir. Under environmental and application conditions, other factors moderate performance (longevity). For the sewer/gel system, these include the amount of time that the gel is exposed to flowing/standing water, the composition of the waters (primarily Trifluralin solubility enhancers; i.e., wetting agents), and spatial position within the pipe with respect to the plant root penetration point (top, bottom).

The performance data derived from FIG. 2 was used to estimate performance under various system parameters. These calculations remain conservative, but are moderated by the practical variables of the system. The critical performance point is the need to maintain 2–5 ppm Trifluralin at the point where the growing plant root would contact the gel barrier or the soils adjacent to the gels. Prior efforts clearly show that Trifluralin is highly effective in preventing root elongation at 2–5 ppm for 95% of the plants tested. A few require 10 ppm Trifluralin to inhibit root growth.

The two values that control the system are reservoir size and release rate for the active. From the experimental study, we used a loading rate or reservoir which contained PE/Trifluralin at 5.2% (w/v), and a Trifluralin load of 7.02% (w/w) TRIFLURALIN, resulting in a reservoir size for Trifluralin of 3710 µg/mL gel (1 $cm^3$). Under these conditions, including 100% saturation with a large water-receiving reservoir, longevities range from 3.3 to 5.5 years. In practice however, the gels would not be exposed to a water reservoir 100% of the time. Using duty cycles (50 and 25%), the time that water would be expected to flow over and puddle over the gel, we can calculate a revised longevity. These range from 4.4 to 7.3 years for a 50% duty cycle, and 9.4 to 15.7 years for a 25% duty cycle.

The portions of the gel that line the top of the pipe can be expected to experience limited bulk water flow events. However, this gel component does experience saturated water vapor at all times. Thus there is a continue loss from the gel to air, and more importantly a likely diffusion of Trifluralin to the lower gel components. Thus we set a typical duty cycle of 10%, with a resulting longevity of 22–36 years.

A moderately conservative duty cycle for an acrylimide treated sewer with the PE/Trifluralin carrier, the 5-year longevity can be attained using a 3% load of PE/Trifluralin based on a Trifluralin content of 0.39% (FIG. 2), but up to 5% PE/TN loads may be necessary where root intrusions are from aggressive plants such as willow and Kudzu.

The use of polyurethane (PU) carriers rather than the polyethylene carriers, results in an increase in Trifluralin reservoir size, and a reduction in Trifluralin release rates. This results in an increase in longevity of the filler gels to 7 years to 15 years. These longevities can be increased based on duty cycles as in the case of the PE gels. For applications where larger cracks in more inaccessible areas of larger sewer lines is a cost and access problem, better performance longevities may be desired, thus the PU/Trifluralin carriers may be preferred. FIG. 2 provides the calculated Trifluralin loading versus longevity.

The other critical parameter, aside from the reservoir and release rate, is the maintenance of a concentration of Trifluralin in both the gels, and in any water-saturated soils adjacent to a pipe leakage area, sufficient to inhibit root growth (5–10 ppm). Additionally, waters flowing over/through the gels will in fact leave the pipe via imperfections (cracks, etc.), and be deposited into adjacent soils. With a minimal release rate of 5 µg TRIFLURALIN/day per cubic cm of gel, Trifluralin would be sufficient to migrate to soils and create an added zone of protection. This could be important for low duty cycle applications, since the half-life of Trifluralin in soils in at least 45 days, and thus its accumulation there would be significant.

The chemical grout products include not only acrylimide gels, but also grouts prepared from N-methylacrylamides and polyacrylamides. In addition, acrylates, epoxies, phenolic resins, and amino resins can form chemical grouts to which Trifluralin-containing pellets can be added. Trifluralin-containing pellets also can be added to such inorganic grouts as silicates that use calcium chloride or formamide as curing agents. These grouts can be used not only for repair but also for soil stabilization in the numerous landscaping applications cited in this application.

The pellets can be made from the polymers that are described in the Pellet section presented just prior to Example 3.

This formulation can be applied by the bladder method described above. In addition, this acrylimide gel can be applied by other means as a preventive measure to prevent root intrusion at pipe joints. It can be used to make grouts and mortars for construction uses. For example, concrete blocks that are joined with mortar or bricks and mortar could benefit from Trifluralin content.

Many polymers other than acrylimide form strong gels used in grouting or soil stabilization. This invention includes other polymer gels that are compatible with TRIFLURALIN. As examples: The polyurethanes of the Bladder Embodiment described above can be considered gels that are useful in grouting. Acrylate gels are quite widely used. Epoxies now are available in gel form. Phenol formaldehyde resins form gels. Lignosulfonates form gels. Inorganic gels that are based on silicate technology were the original grouts and soil stabilizers. They could be improved by use of Trifluralin in pellet formulations to extend the longevity of the product.

Pavement Protection

Pavements include, inter alia, sidewalks, streets, highways, runways, walkways in landscapes, etc. Gaps in pavements occur frequently. They result from many causes, including freeze thaw damage, mechanical damage by people or vehicles using the pavement, mistakes in construction of the pavement, and intentional spaces as part of the landscape design.

Plants invade pavement gaps, exacerbating damage and spoiling esthetic values. Many patents have issued on approaches to protect pavements from these problems. A relevant patent is Van Voris, et al., U.S. Pat. No. 5,898,019, which covers Trifluralin in a polymer matrix. The composition may contain carbon black.

Attainment of sustained release of Trifluralin that is applied to gaps in pavements can be improved by using a clay/Trifluralin/polymer composite material. It can be made by sorbing Trifluralin into clay (e.g., montmorillonite) that is in colloidal form. The colloidal state is essential for best performance in longevity and reduced Trifluralin degradation, compared with carbon black and other fillers presented in the prior art.

The sorption process can use Trifluralin vapor that contacts and permeates into the tiny clay particles. A fluidized bed process is especially convenient for loading the particles. However, molten or dissolved Trifluralin also can be used for loading. The loaded clay is incorporated into a polymer matrix that is preferably polypropylene or polyethylene or polyester (e.g., PET). The composite material can be applied to the gaps in the pavement directly or as part of a product that includes a sealant.

Gaskets that Contain Trifluralin

The weakest point of resistance to plant root intrusion frequently is the seal between lengths of pipe. Gaskets that join the pipes usually are made of elastomeric materials. Incorporation of Trifluralin into gasket materials has been described by Cataldo and coworkers in U.S. Pat. No. 5,449,250. Longevity and effectiveness in preventing root intrusion at the gasket is attained in this invention by using a clay/trifluralin/elastomer composite material. It can be made by sorbing Trifluralin into clay (e.g., montmorillonite) that is in colloidal form. The colloidal state is essential for best performance in longevity and reduced Trifluralin degradation, compared with carbon black and other fillers presented in the prior art.

The sorption process can use Trifluralin vapor that contacts and permeates into the tiny clay particles. A fluidized bed process is especially convenient for loading the particles. However, molten or dissolved Trifluralin also can be used for loading. The loaded clay is incorporated into an elastomer matrix that is preferably butyl rubber, neoprene rubber, silicone elastomer, thermoplastic urethane elastomer, or other polymeric gasket material.

Embodiment #2

Barrier Coating Embodiment

Modify a geotextile fabric by applying a barrier coating that contains TRIFLURALIN. The barrier coating (e.g., thermoset) could be an unsaturated polyester or an epoxy resin.

Many landscape applications make use of geotextile fabrics that are made from cheap polyolefins (polyethylene, polypropylene) or recycled PET from soda pop bottles. There are three ways to put Trifluralin into a geotextile:

incorporate Trifluralin while making the fabric; infuse Trifluralin into the fabric; and put Trifluralin into a barrier coating that is adhered to the fabric.

Barrier coatings and films are frequently used to control the release of active ingredients. They usually are Saran® materials that are satisfactory for medical and veterinary uses. However, they are much too expensive for the intended landscape applications. Therefore, a "poor man's Saran®" is the product to be used in this invention.

The two most promising candidates are unsaturated polyesters and epoxies. They are cheap, available, durable, and capable of trapping and holding Trifluralin strongly so that release is slow.

Unsaturated polyesters are very familiar products. Glass fiber reinforced plastics (e.g., Fiberglas® products) combine glass fiber with unsaturated polyesters to produce boat hulls, automobile body panels, etc. Geotextile fabrics are made of a polyester or polyolefins, instead of glass fibers, but there is a good analogy here.

Figure 4:
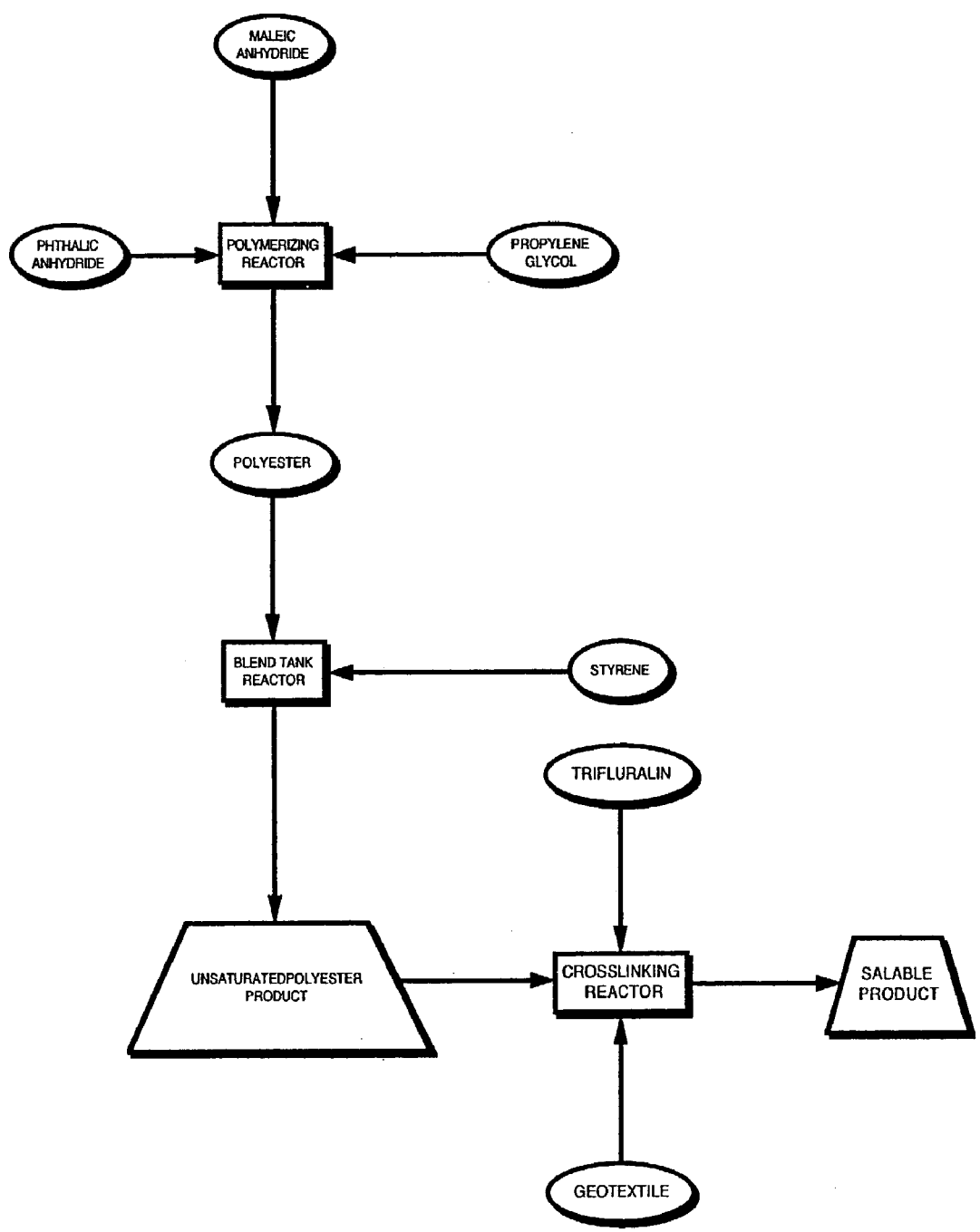
FIG. 4 schematically depicts the manufacturing steps for the unsaturated polyester barrier embodiment of the present invention.

Unfilled unsaturated polyesters also are used in cheap coatings in which high performance, such as pigmented coatings for marking highways, is required. Thus, this class of polymers is durable in bad weather and can withstand mechanical punishment. Because of the current applications cited above, unsaturated polyesters can provide rugged coatings that are heavily crosslinked so that Trifluralin can be trapped in a barrier matrix. FIG. 4 is a flow sheet for production and use of unsaturated polyesters for sustained release of TRIFLURALIN. The production process would consist of blending Trifluralin with a mixture of purchased unsaturated polyester (e.g., phthalic anhydride, maleic anhydride, and propylene glycol) and styrene. An initiator (e.g., a peroxide) is added as the mixture is coating the geotextile. The coated geotextile is heated enough to cause crosslinking. Needle punching is used to establish pathways for movement of water through the geotextile.

The next issue is whether the Trifluralin can be released at a rate that is slow enough to be useful for the intended landscape applications. U.S. Pat. No. 5,985,010 describes an animal repellent composition in which pepper extract is combined with various cross-linkable coating materials, such as synthetic rubber, natural rubber, epoxies, paint, and sealants. Wires are coated with this material to produce a product that repels rodents, such as rats, mice, and squirrels. Multilayer coatings were used to increase product life.

The animal repellent data show that these coatings have the type of flexibility that is needed. These data also show that these coatings store a significant amount of active ingredient. Note that the target for this repellent is an animal that differs greatly from a plant root and that the chemical structure of the pepper extract is very different from TRIFLURALIN.

U.S. Pat. Nos. 5,733,848 and 5,883,046 describe the specific use of unsaturated polyesters for microencapsulation of agricultural chemicals, especially herbicides. This prior art establishes that herbicides are able to diffuse slowly through selected unsaturated polyesters. Note, that there is a very real difference between herbicide in a microcapsule and herbicide in a coating. The microcapsule is a container in which countless herbicide molecules are in a continuous phase while herbicide molecules are trapped in the coating matrix in a barrier coating so that there is not any continuous phase of active ingredient.

Figure 5:
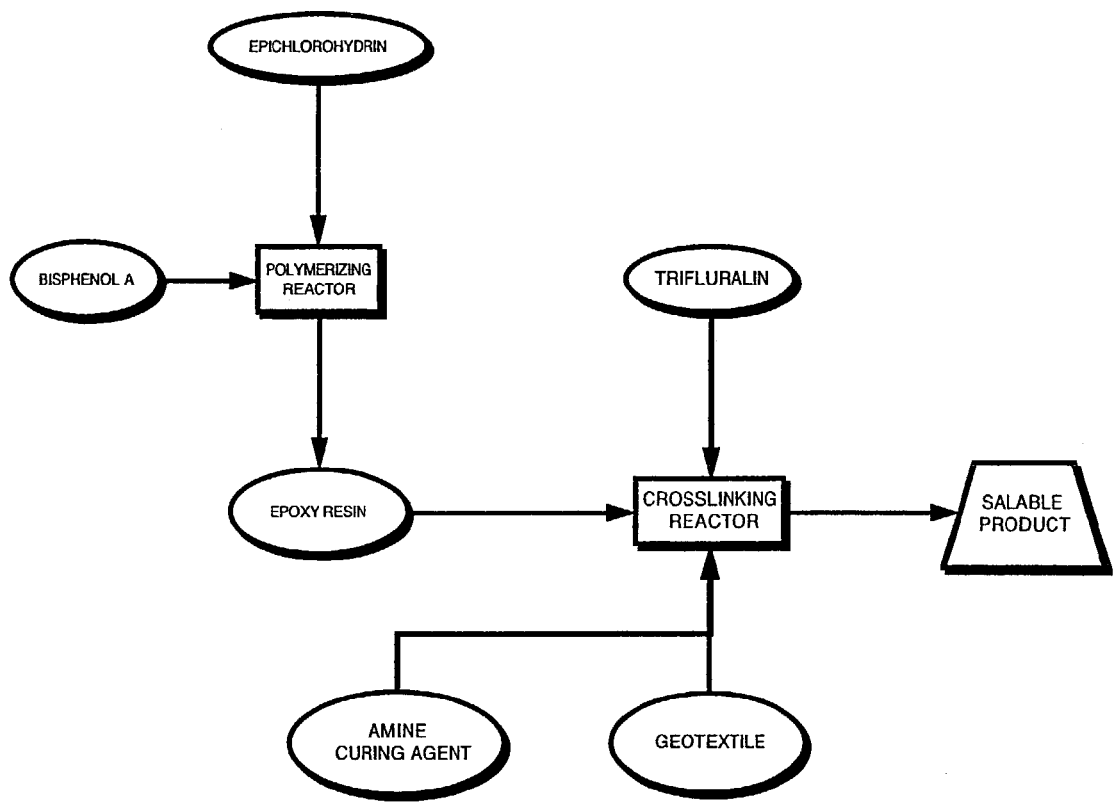
FIG. 5 schematically depicts the manufacturing steps for the epoxy resin barrier coating embodiment of the present invention.

Epoxy resins are thermoset polymers that are used to make protective coatings that have excellent barrier properties and are noted for their durability in severe environments. FIG. 5 shows a flow sheet for production of geotextiles that use epoxy coatings that are reservoirs for TRIFLURALIN. Liquid epoxy resins would be blended with molten Trifluralin or a solution (in toluene) of TRIFLURALIN. An amine curing agent would be added and the coating would be applied to the geotextile and cured in place.

Technical feasibility for epoxy resins as barrier coatings that can release insecticides has been established by Cataldo and Van Voris' experiments, as shown in U.S. Pat. Nos. 5,985,304 and 5,801,194. The results showed that the release rate was about 10% as great as that of other reservoir materials. The chemical structures of the tested insecticides were very different from the 2,6-dinitro-aniline structure of TRIFLURALIN.

EXAMPLE 4

Dow epoxy resin (DER, Dow Epoxy Resin, Dow Chemical Co., Midland, Mich.) 331 is dissolved toluene and mixed with a solution that contains GENAMID 235 and VERSAMID 115 and Trifluralin in methyl isobutyl ketone. The quantities of the epoxy resin and the two curing agents are 1-to-1 on a molar equivalent basis. After 15 minutes of stirring, the viscosity and temperature are within the normal range for room temperature spraying. The solution is sprayed onto a polypropylene geotextile. The solvent evaporates while the epoxy resin cures. The coating that results slowly exudes Trifluralin over a period of several years.

Embodiment #3

Geotextile Modification Embodiment

In this embodiment of the present invention, modification of a geotextile to incorporate Trifluralin can be accomplished in three ways:

Infusion

Figure 6:
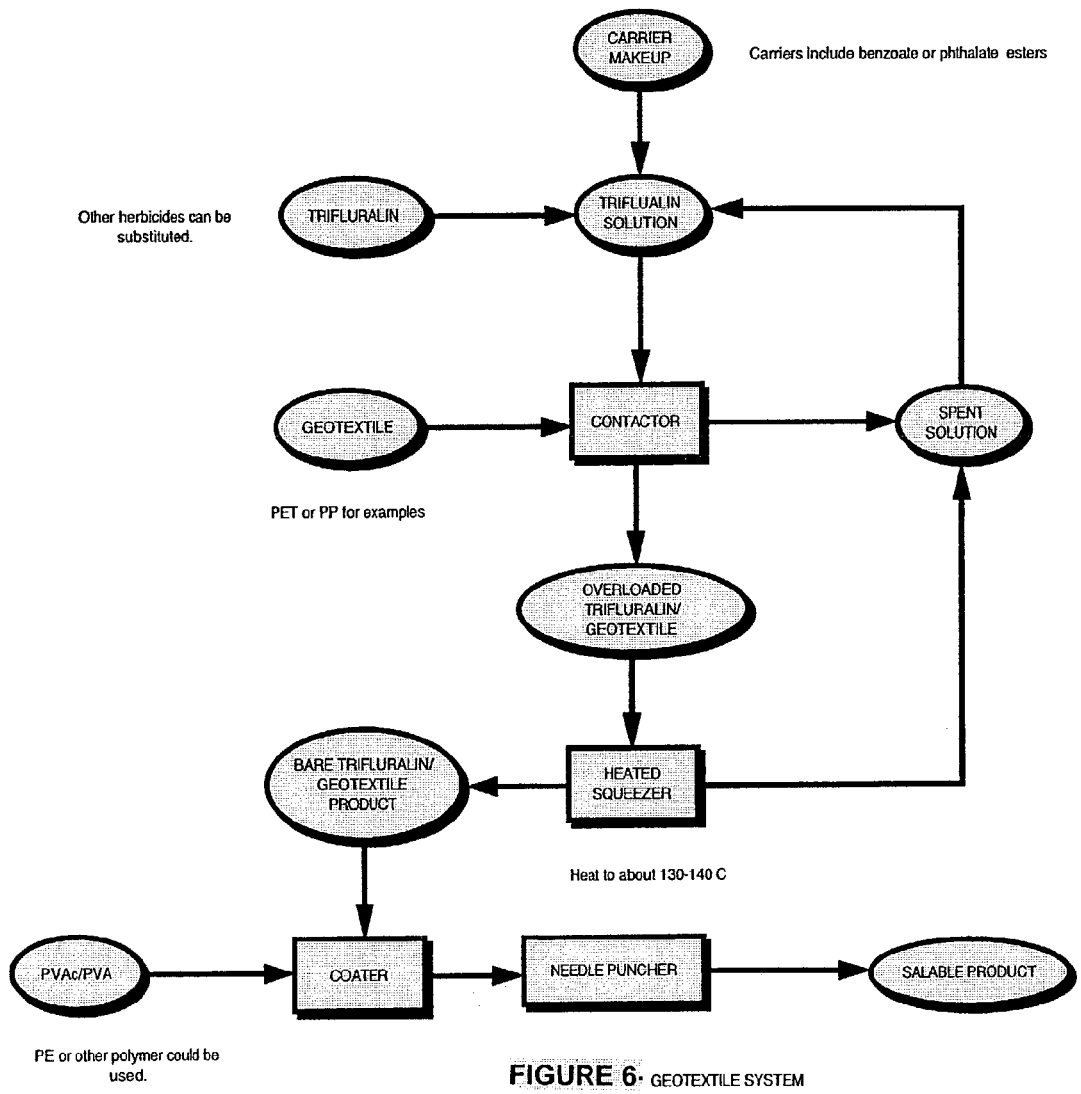
FIG. 6 schematically depicts the manufacturing steps for the geotextile embodiment of the present invention.

A solution of a carrier (e.g., benzoate or phthalate esters) and a herbicide (e.g., TRIFLURALIN) is formed and contacted with a geotextile (e.g., polypropylene or PET) to the point of over-saturation (FIG. 6). The overloaded geotextile/herbicide is subjected to heat (e.g., 130°–140° C.) squeezing (pressure) to produce a bare geotextile impregnated product, which then is overcoated with a polymer (e.g., PVA/PVAc copolymer) to make the product safer to handle and easier to install. Needle punching of this product is required after the infusion of the geotextile has been completed such that the final product will allow water and air to pass through it much like the commercially available landscape fabrics. This product is intended to have sustained release properties (e.g., 15+years) for wrapping sewer line or sidewalks, to avoid root damage from woody plants. Trifluralin concentrations of about 3.5–4 oz of the polymer pre-processing formulation per square yard are desired for this product. In addition to these two applications, control of plant/root growth in landscaped areas, roadside gravel areas, planter strips, stone walkways, brickwork patios and driveway can be treated by this method.

EXAMPLE 5

Experiments were conducted in which Trifluralin was dissolved in a plasticizer/solvent, such as, methyl benzoate. This solution is contacted with a geotextile fabric that sorbs the mixture into its fibers. Then, most of the plasticizer is removed from fibers by heating and pressure. Some of it is retained within the geotextile and as a film that surrounds the fibers. The concentration can be increased by increasing both temperature and duration of the exposure of the geotextile to the solution.

Typical results are shown in the table below.

Plasticizer Loading of Polymers and Release Rates

| Material | Loading | Release |
|----------|---------|---------|
| PET | 20–40% | 6–12 $\mu g/cm^2/day$ |
| PP | 30–50% | 50–90 $\mu g/cm^2/day$ |
| PE | 12–25% | 15–22 $\mu g/cm^2/day$ |

* plasticizer affects release rates (increase)
* barrier films can reduce release rate by factor of 12–30.

This embodiment is analogous to one of the technologies now used to dye polyester fibers and fabrics. Therefore, it has technical feasibility in placing some Trifluralin into the fibers.

The infusion embodiment can be improved. The geotextile fabric that contains Trifluralin could be coated with a barrier coating to reduce the rate of release of this herbicide. This revised embodiment also would put to use the Trifluralin that adheres to the surface of the fibers.

The choice of barrier coating would depend on cost considerations that usually preclude use of SARAN (PVdC) coatings or laminations. The barrier coatings that are more promising include the same unsaturated polyesters and epoxies that were discussed in the previous section of this report. These barrier coatings could contain TRIFLURALIN.

The modified embodiment could allow for more storage of Trifluralin per unit area. This extra storage might be needed to attain a goal of product longevity that could not be reached by fiber infusion alone or loaded-barrier coating alone.

Polyethylene Cord Embodiment

An infusion embodiment was generated in which commercially available polyethylene cord was infused with Trifluralin to obtain a loading of about 10% to 20%. The product is intended to maintain a vapor pressure of Trifluralin that is high enough to inhibit root intrusion.

EXAMPLE 6

The purpose of this example was to determine whether Trifluralin contained within polyethylene (PE) cords could transfer in the vapor state in sufficient quantities to transfer Trifluralin to wetted surfaces within the sewer line, particularly upper surfaces not in contact with periodic flowing waters. The objective was to suspend a Trifluralin delivery system (cord over long lengths of sewer pipe), and use this as a delivery means to inhibit root growth and/or re-penetration by transfer of Trifluralin to the growth region of roots. Aged cord containing 20% Trifluralin in PE was used.

Methods

Twelve (12) cm sections of ¼ inch extruded PE cord containing 20% Trifluralin (w/w) were suspended over 500 mL of two solutions contained within 1 L capped bottles. The cords were lightly washed with 90% MeOH to remove crystalline Trifluralin surface deposits. The receiving solutions consisted of either water wetted with 0.1% Tween 20® or 80% MeOH. The cord was suspended approximately 6 cm from the solution surfaces.

At periodic intervals sub-samples were removed and analyzed by HPLC to determine Trifluralin accumulations. This continued until apparent steady state is reached, or when daily rates were constant.

Results and Discussion

FIG. 7 provides the release profiles over the 16-day study period. As noted, release rates, as determined by vapor transfer from the cord surface to the solutions ranged from 500 to 50 $\mu g$ TRIFLURALIN/day for MeOH solutions; for water containing wetting agent, values ranged from 80 to 20 $\mu g$ TRIFLURALIN/day. The differences over the 16-day period reflect simply the repletion of readily diffusible Trifluralin from the near surface of the cords. The difference between the two receiving solutions reflects the relative solubilities of the Trifluralin in the two solutions, and is affected by the rate at which the Trifluralin can be removed from the air (by receiving surfaces), and the rate of vapor replenishment from the cord/reservoir.

It is fully expected that these rates will decline over time frames of years, due to loss of Trifluralin from the near-surface of the reservoir/cord. Overall longevity of the system tested was estimated at approximately 44 years.

Infusion with Carrier Polymerization

This embodiment differs from the infusion embodiment in that the carrier is polymerizable (FIG. 8) and following the heat squeezing operation is subjected to polymerization (e.g., UV or free-radical catalyst). The overcoating step may be unnecessary in this embodiment. Alternatively, a barrier coating that also contains Trifluralin could be used with this embodiment.

Much of the technical and cost problems of infusion embodiment arise from the difficulties in removal of plasticizer from the fiber without loss of undue amounts of Trifluralin and the degradation of the strength of the fabric due to plasticizer presence.

A novel solution involving the polymerization of the plasticizer that remains within the fiber (FIG. 8) has been developed. Thus, a plasticizer is chosen that also is a monomer. It was determined that Trifluralin is quite soluble in ethyl methacrylate and lauryl methacrylate. Experiments indicated that these plasticizer/monomers are capable of carrying Trifluralin into PET fibers. Thus, technical feasibility is evident up to this point in the process.

The next step is to polymerize the methacrylate monomer that is within the fiber, using either UV radiation (preferred) or peroxide (if necessary). Polymerization of a monomer that is dissolved in a polymer matrix is well known in the polymer art as producing "interpenetrating polymer networks" (IPN). Therefore, technical feasibility that an IPN can be formed is assured. The formation of the IPN may allow the overcoating step to be omitted, which would be desirable.

V. Embodiment #4

Fiber Incorporation Embodiments

The two fiber incorporation aspects of this invention are incorporation during melt spinning and incorporation into hollow fibers.

Incorporation During Melt Spinning

This embodiment involves the manufacture of geotextile fabrics that contain TRIFLURALIN. The herbicide would be incorporated into the fibers during their production, for example, via melt spinning or spun bonding techniques. The products would compete with the BioBarrier® family of products.

The manufacture of geotextiles from polypropylene or PET or polyethylene is a melt spinning operation. Therefore, it is logical to consider adding Trifluralin to the melted polymer prior to fiber/fabric production (FIG. 9).

The result would be a fiber that already contains the herbicide. The messiness of the infusion method of getting Trifluralin into the fiber is avoided. Use of a plasticizer is avoided.

The melt spinning or spun bonded processes that are used to make geotextiles use spinnerets with tiny holes through which the melt must pass. Clogging of these holes is a nightmare that geotextile producers work to avoid because of the downtime that results. Thus, addition of Trifluralin to the melt must yield a true solution or a dispersion of particles that are so small that they pass through the holes easily.

Geotextile fabrics must meet rigorous standards of strength, flexibility, and durability. Mechanical performance tests help to determine the capacity of the polymer—that is the percentage of Trifluralin that can be stored in the fibrous product. There is a related hurdle involved, which is the change in the mechanical properties of the fibers as the Trifluralin filler is released over time. A third technical parameter is the rate at which Trifluralin is released from the fibers, with the goal being a slow rate. There is a high probability that the fibers would require a barrier coating to reach the rate goal.

Unlike the other embodiments, fiber spinning subjects Trifluralin to high temperatures that could result in a hazardous work environment. The manufacturer would need to install special environmental safety equipment and take suitable precautions. Many companies handle hazardous vapors all of the time.

This aspect of the present invention overcomes these hurdles by use of one or more of the following methods:
1. Sorption of Trifluralin onto tiny carrier particles that can pass through the spinnerettes that are used for melt spinning. The carriers of use in this embodiment of the invention include polymer particles (e.g., epoxies and unsaturated polyesters) or colloids that are based on clays (especially montmorillonites) or silica (especially via sol gel processes), or alumina or carbon.
2. Choice of a polymer with a solubility parameter close to that of Trifluralin to assure solubility of the active ingredient in the polymer melt;
3. Use of melt spinning technologies that minimize the likelihood of spinneret clogging (e.g., electrostatic spinning).
4. Production of geotextile fabrics in which the TRIFLURALIN-loaded fibers constitute only a fraction of the total fibers in the product. The majority of the fibers will be those that contribute to the strength and other mechanical properties, while only the minimum percentage of the more expensive TRIFLURALIN-loaded fibers is used.
5. Control of release rate is obtained by use of appropriate polymer coatings.

The art reported in the Art section shows that dyes, for example, can be incorporated into polymer melts and spun into fiber form, thus confirming that this general embodiment is viable.

Incorporation into Hollow Fibers

This embodiment can be described as follows: Use hollow polypropylene or PET or polyethylene fibers as a reservoir for TRIFLURALIN. Transfer a melt of Trifluralin into this cavity using capillary action, vacuum, or pressure. The transfer may also be accomplished by use of a solution of Trifluralin in a volatile organic solvent. Use these fibers as some or all of the fibers in a geotextile product that would be made under a special contract with a geotextile producer. FIG. 10 sketches this process embodiment.

Hollow polypropylene or PET fibers are available now that are rugged and durable. They are air-filled and used as insulation in sleeping bags. The high quality of the sleeping bag product is not needed, but it does demonstrate the technical and commercial feasibility of basing this invention on hollow fibers. The particular hollow fiber product needs to be selected with respect to the diameter of the cavity and the thickness of the wall. Recycle PET would help to reduce costs and be more environmentally responsible.

Hollow fiber membranes are employed to transport liquids. The most suitable process for filling the fiber cavity will depend on the capillary behavior between molten Trifluralin (or Trifluralin solution) and the fiber wall. This loading process can be accomplished at relatively low temperature, in contrast to the fiber melt spinning embodiment.

These fibers could be incorporated into (or onto) a spun bonded sheet. Alternatively, a nonwoven fabric could be made from these fibers, mixed with other fibers. The other fibers can provide strength and other mechanical properties, while reducing the cost of the product. The nonwoven sheet could be coated with a barrier coating, if it is needed. The product could be needle punched to provide a geotextile.

While the invention has been described with reference to a preferred embodiment, those skilled in the art will understand that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. In this application all units are in the metric system and all amounts and percentages are by weight, unless otherwise expressly indicated. Also, all citations referred herein are expressly incorporated herein by reference.

We claim:

1. A method for protecting pipe from one or more of root intrusion or root growth when said pipe is placed underground, comprising the steps of:
    (I) providing a pumpable coating formulation of:
        (a) a 2,6 dinitroaniline herbicide;
        (b) a polymer pellet impregnated with a 2,6-dinitroanililne herbicide-colloidal sorbed clay; and
        (c) a film-forming polymer;
    (II) inflating a bladder inside of said pipe to create a space near an inside wall of said pipe; and
    (III) pumping a coating into said space and permitting said coating to polymerize.

2. The method of claim 1, wherein said polymer of said polymer pellet is one or more of a polyurethane, a polyethylene, a polypropylene, a polyester, an epoxy, a phenolic, an amino resin, a silicone, a lactic acid polymer, a cellulosic polymers, or lignin.

3. The method of claim 2, wherein said polymer of said polymer pellet is one or more of high density polyethylene, linear low density polyethylene, low density polyethylene, polyethylene terephthalate, natural rubber, synthetic rubber, nylon, cellulose, cellulose acetate, cellulose acetate butyrate, carboxymethyl cellulose, hydroxypropyl cellulose, thermoplastic polyurethane, thermoset polyurethane, or a water-curable polyurethane.

4. The method of claim 1, wherein said film-forming polymer is a polyurethane.

5. The method of claim 1, wherein said colloidal clay is one or more of montmorillonite or bentonite.

6. A method for protecting pipe from one or more of root intrusion or root growth when said pipe is placed underground, comprising the steps of:
(a) infusing a cord with a 2,6-dinitroaniline herbicide;
(b) hanging said infused cord inside said pipe,
whereby vapors released from said infused cord protect said pipe from one or more of root intrusion or root growth.

7. The method of claim 6, wherein said cord is a polyethylene cord.

8. In a melt spinning process for manufacturing a geotextile wherein molten fiber-containing polymeric material is melt spun using spinnerets, the improvement which comprises the steps of:
blending particles bearing a 2,6-dinitroaniline herbicide with a melt of said polymeric material, the size of said particles allowing the blend to be melt spun.

9. The process of claim 8, wherein said polymeric material is one or more of a polyethylene, a polypropylene, or a polyethylene terephthalate.

10. The process of claim 8, wherein said particles are one or more of an epoxy, an unsaturated polyester, or a clay.

11. The process of claim 8, wherein said clay is a montmorillonite or bentonite clay.

12. The process of claim 8, wherein solubility parameter of the 2,6-dinitroaniline herbicide and the polymeric material are sufficiently close to ensure dissolution of said 2,6-dinitroaniline herbicide in said melt.

13. The process of claim 8, wherein said geotextile is coated with a barrier coating to retard release of said 2,6-dinitroaniline herbicide therefrom.

14. The process of claim 8, wherein said polymeric material is electrostatically spun.

15. An improved geotextile fabric, which comprises:
incorporated into said geotextile fabric is a formulation of:
hollow fibers containing a 2,6-dinitroaniline herbicide.

16. The improved geotextile fabric of claim 15, wherein said hollow fibers are subjected to one or more of capillary action, vacuum, or pressure to fill said fibers with said 2,6-dinitroaniline herbicide.

17. The improved geotextile fabric of claim 15, wherein said fibers are one or more of polyethylene hollow fibers or polyethylene terephthalate hollow fibers or polypropylene hollow fibers.

18. An improved geotextile fabric, which comprises:
dispersed within said geotextile fabric is a formulation of:
(a) a 2,6-dinitroaniline herbicide; and
(b) a polymer pellet impregnated with a 2,6-dinitroanilne herbicide-sorbed colloidal clay.

19. The geotextile fabric of claim 18, wherein said geotextile fabric is made from one or more of an unsaturated polyester, an epoxy, a polyolefin, polyethylene terephthalate, or recycled polyethylene terephthalate.

20. The geotextile fabric of claim 18, wherein said formulation also is coated onto said geotextile fabric.

21. The geotextile fabric of claim 18, wherein said colloidal clay is one or more of montmorillonite or bentonite.

* * * * *